United States Patent
Brannon et al.

(10) Patent No.: US 11,801,384 B2
(45) Date of Patent: Oct. 31, 2023

(54) METHOD FOR CALIBRATION OF TRANSCUTANEOUS NERVE STIMULATOR

(71) Applicants: Ami Brannon, West Palm Beach, FL (US); Kermit Falk, West Palm Beach, FL (US); Vincent Manopoli, West Palm Beach, FL (US)

(72) Inventors: Ami Brannon, West Palm Beach, FL (US); Kermit Falk, West Palm Beach, FL (US); Vincent Manopoli, West Palm Beach, FL (US)

(73) Assignee: NEUVANA, LLC, West Palm Beach, FL (US)

(*) Notice: Subject to any disclaimer, the term of this patent is extended or adjusted under 35 U.S.C. 154(b) by 233 days.

(21) Appl. No.: 17/498,390

(22) Filed: Oct. 11, 2021

(65) Prior Publication Data
US 2022/0111205 A1    Apr. 14, 2022

Related U.S. Application Data

(60) Provisional application No. 63/090,496, filed on Oct. 12, 2020.

(51) Int. Cl.
*A61N 1/36* (2006.01)
*A61N 1/04* (2006.01)

(52) U.S. Cl.
CPC ....... *A61N 1/36034* (2017.08); *A61N 1/0456* (2013.01); *A61N 1/36031* (2017.08)

(58) Field of Classification Search
CPC .............. A61N 1/36034; A61N 1/0456; A61N 1/36031; A61N 1/0551; A61N 1/36003; A61N 1/36017
See application file for complete search history.

(56) References Cited

U.S. PATENT DOCUMENTS

2006/0229687 A1* 10/2006 Goetz ................ A61N 1/36185
                                                                    607/66
2008/0033510 A1    2/2008 Derregraven et al.
(Continued)

OTHER PUBLICATIONS

Kela Casey—Let Us Understand Searching Algorithms—https://codersera.com/blog/let-us-understand-searching-algorithms—Aug. 5, 2020.
(Continued)

*Primary Examiner* — Amanda K Hulbert
*Assistant Examiner* — Natasha Patel
(74) *Attorney, Agent, or Firm* — Lott & Fischer, P.L.

(57) ABSTRACT

Method for calibrating a nerve stimulation device comprising (a) providing the user with an initial stimulus at a sub-sensory level and obtaining feedback regarding whether the stimulus is felt; (b) if it is not felt, increasing the stimulation level by a first level variation and again obtaining feedback; (c) repeating the previous step until feeling the stimulus is reported; (d) reducing stimulus by the initial level variation; (e) repeating the process from the previously established level while using a second level variation is used which is smaller than the first level variation; (f) once stimulus feeling is reported, the level is again reduced by the second level variation; (g) this level, achieved after the second "crossing" of the threshold, can be used as the sensory threshold value; (h) additional calibration rounds can be conducted using ever-lower level variations for each subsequent round to more accurately the sensory threshold is determined.

5 Claims, 8 Drawing Sheets

| Step | Stimulation Level | Level Variation (to be applied at next iteration) | User Reports Feeling Stimulus? |
|---|---|---|---|
| 1 | 0 Volts | First (7 Volts) | No |
| 2 | 7 Volts | First (7 Volts) | No |
| 3 | 14 Volts | First (7 Volts) | No |
| 4 | 21 Volts | Second (1 Volt) | Yes (decrease level by 7 volts) |
| 5 | 14 Volts | Second (1 Volt) | No |
| 6 | 15 Volts | Second (1 Volt) | No |
| 7 | 16 Volts | Third (0.25 Volt) | Yes (decrease level by 1 volt) |
| 8 | 15.0 Volts | Third (0.25 Volt) | No |
| 9 | 15.25 Volts | Third (0.25 Volt) | No |
| 10 | 15.5 Volts | Third (0.25 Volt) | Yes (decrease level by 0.25 volts) |
| 11 | 15.25 | N/A | N/A |

(56) References Cited

U.S. PATENT DOCUMENTS

| | | | |
|---|---|---|---|
| 2014/0188402 A1* | 7/2014 | Garcia | G01N 33/48792 |
| | | | 702/23 |
| 2017/0281958 A1 | 10/2017 | Serrano Carmona et al. | |
| 2019/0001129 A1* | 1/2019 | Rosenbluth | A61N 1/08 |
| 2019/0046800 A1 | 2/2019 | Doan et al. | |
| 2019/0209844 A1 | 7/2019 | Esteller et al. | |
| 2020/0179694 A1* | 6/2020 | Kong | A61N 1/0484 |

OTHER PUBLICATIONS

International Application No. PCT/US21/54397—Patent Cooperation Treaty PCT International Search Report—Completed Dec. 16, 2021 (dated Jan. 24, 2022).

International Application No. PCT/US21/54397—Patent Cooperation Treaty PCT Written Opinion of the International Searching Authority—Completed Dec. 16, 2021 (dated Jan. 24, 2022).

\* cited by examiner

| Step | Stimulation Level | Level Variation (to be applied at next iteration) | User Reports Feeling Stimulus? |
|---|---|---|---|
| 1 | 0 Volts | First (7 Volts) | No |
| 2 | 7 Volts | First (7 Volts) | No |
| 3 | 14 Volts | First (7 Volts) | No |
| 4 | 21 Volts | Second (1 Volt) | Yes (decrease level by 7 volts) |
| 5 | 14 Volts | Second (1 Volt) | No |
| 6 | 15 Volts | Second (1 Volt) | No |
| 7 | 16 Volts | Third (0.25 Volt) | Yes (decrease level by 1 volt) |
| 8 | 15.0 Volts | Third (0.25 Volt) | No |
| 9 | 15.25 Volts | Third (0.25 Volt) | No |
| 10 | 15.5 Volts | Third (0.25 Volt) | Yes (decrease level by 0.25 volts) |
| 11 | 15.25 | N/A | N/A |

FIG. 1

| Step | Stimulation Level | Level Variation (to be applied at next iteration) | User Reports Feeling Stimulus? |
|---|---|---|---|
| 1 | 0% | First (+5%) | No (seeking 'Yes') |
| 2 | 5% | First (+5%) | No (seeking 'Yes') |
| 3 | 10% | First (+5%) | No (seeking 'Yes') |
| 4 | 15% | First (+5%) | No (seeking 'Yes') |
| 5 | 20% | First (+5%) | No (seeking 'Yes') |
| 6 | 25% | First (+5%) | No (seeking 'Yes') |
| 7 | 30% | First (+5%) | No (seeking 'Yes') |
| 8 | 35% | First (+5%) | No (seeking 'Yes') |
| 9 | 40% | First (+5%) | No (seeking 'Yes') |
| 10 | 45% | First (+5%) | No (seeking 'Yes') |
| 11 | 50% | First (+5%) | No (seeking 'Yes') |
| 12 | 55% | First (+5%) | No (seeking 'Yes') |
| 13 | 60% | First (-5%) | Yes |
| 14 | 55% | Second (+2%) | No (seeking 'Yes') |
| 15 | 57% | Second (+2%) | No (seeking 'Yes') |
| 16 | 59% | Second (-2%) | Yes |
| 17 | 57% | Third (+1%) | No (seeking 'Yes') |
| 18 | 58% | Third (-1%) | Yes |
| 19 | 57% | Fourth (+0.5%) | No (seeking 'Yes') |
| 20 | 57.5% | Fourth (-0.5%) | Yes |
| 21 | 57% | Completed | N/A |

METHOD FOR CALIBRATION OF TRANSCUTANEOUS NERVE STIMULATOR

This application is being filed as a non-provisional patent application under 35 U.S.C. § 111(a) and 37 CFR § 1.53(b). This application claims priority under 35 U.S.C. § 119(e) to U.S. provisional patent application Ser. No. 63/090,496 filed on Oct. 12, 2020, the contents of which are incorporated herein by reference.

FIELD OF INVENTION

The invention relates generally to the field of electrical stimulation devices. The present disclosure relates to methods of electrical stimulation of anatomic structures such as nerves, blood vessels, muscles, connective tissue, glands, individual organs, and organ systems and devices that accomplish such stimulation using modulated electric current applied directly or indirectly to tissue through external (non-invasive) or minimally invasive measures. In particular, the present disclosure relates to methods for calibrating devices that use transcutaneous and percutaneous methods of stimulating the vagus (X) nerve and other nerves, such as the trigeminal (V), facial (VII), vestibulocochlear (VIII), and glossopharyngeal (IX).

BACKGROUND

The use of electric current to stimulate nerves and other anatomic structures can have positive therapeutic benefits. Devices, such as those described in U.S. Pat. Nos. 10,828,461 and 11,103,693, issued to Applicant and incorporated herein by reference, provide such benefits through devices providing transcutaneous electrical stimulation of the vagus nerve (hereinafter Vagus Nerve Stimulation or "VNS").

In particular, the above-referenced devices accomplish electrostimulation of the vagus nerve using modulated electric signals applied directly or indirectly to human or animal anatomic targets through external (non-invasive) measures. In particular, the devices provide neuromodulation by transcutaneously stimulating anatomic targets to cause an array of therapeutic benefits depending on where the stimulation is directed.

Various embodiments of these devices are described in the above-referenced patents to provide electrostimulation at areas on the same side of the cranium, for example, a pair of electrodes on the left or right side of the user's head. Other embodiments can have electrodes placed on both sides of the user's head, but each respective electrode pair (or set) is only on one side of the user's head. Finally, further embodiments can place the two or more poles of a respective electrode pair or set on opposing sides of the user's head to deliver trans-cranial electrical stimulation.

One such exemplary device utilizes a non-implanted signal generator connected (by wire or wirelessly) to a user coupler located on the user's ear. As used herein, a user coupler, a patient coupler, an electrode coupler, a user coupling device, or a device coupler all are devices that place the electrodes adjacent the tissue to be electrically stimulated. In one exemplary embodiment, the user coupler places electrodes adjacent the auricular branch of the vagus nerve. In other embodiments, the user coupler places electrodes adjacent to the trigeminal nerve. Various advantages of the user couplers described herein is that they are able to be used on varying overall ear anatomies by taking advantage of various anatomical features including consistent anatomical features that are universal across a large portion of the population, they are able to maintain consistent and adequate contact during daily activities, they have a progressive look, they are comfortable, and they are not dependent on occluding the auditory canal to allow other auditory canal systems (e.g., speakers for music) to function simultaneously.

With respect to such devices, it is often necessary to calibrate the device to a specific user in order to deliver the appropriate amount of electrical stimulation to the targeted region. This is so because when the electrical stimulation level is too low, the device may not be delivering the optimal amount of therapy. Conversely, when the level is too high the user may experience discomfort.

Of similar importance is the fact that studies have demonstrated that VNS operates at both the sensory and sub-sensory level. It is sometimes desirable to operate these devices at a level that is just below the sensory level of the user. It is particularly useful to operate at these levels when conducting single or double-blind trials that include a test group and a control group in order to account for a "placebo" effect. In such trials the control group is provided no nerve stimulation, or stimulation with characteristics, such as modulation, that are different from the test group. The test group is provided stimulation at a determined level and which characteristics that are the subject of the trial. By administering stimulation at the sub-sensory level, the test subjects are unaware (or "blind") as to whether they are in the test or control group since neither group senses the simulation.

Moreover, in order to achieve the most effective therapeutic results, stimulation should be delivered at a level that is in the sub-sensory range but is very close to the threshold between sensory and sub-sensory (hereinafter the "Sensory Threshold" or "ST.") This level, however, varies depending on each user and their physiological state and structure. Therefore, for optimal benefits, the VNS device should be calibrated specifically for the user. This is a process that heretofore has been difficult and time consuming.

No programmed strategies are known to Applicant for measuring the Sensory Threshold for a particular user, and none that can be used solely by the user. The use of a built-in "thresholding" strategy that calibrates a device is of significant value. Once determined, the Sensory Threshold output can then be associated with a user to create a dynamic technique which reduces the time required to reestablish or reconfirm the ST value for that user in subsequent sessions.

It is therefore desirable, and the object of the present invention, to provide an efficient method for calibrating a VNS device to establish a Sensory Threshold level for a user.

SUMMARY OF INVENTION

The method for calibrating the VNS device involves providing the user with an initial stimulus at a level low enough to presume it is sub-sensory and requesting or obtaining feedback from the user regarding whether the stimulus can be felt. If the user's feedback reports no feeling, the stimulation level is increased by a first level variation and the feedback is again requested. This process is repeated until the user reports feeling the stimulus, the level is then reduced by the initial level variation.

The process is then repeated from the previously determined level except that a second level variation is used which is higher resolution (smaller interval) than the first level variation. Once the user reports feeling the stimulus, the level is again, reduced by the second level variation. This level, achieved after the second "crossing" of the threshold, can be used as the ST value. However, additional calibration rounds can be conducted hereafter using ever-lower-level variations for each additional round. The more rounds that are conducted, the more accurately the ST will be determined.

Accordingly, disclosed is a method for calibrating a nerve electrostimulation device, the method comprising the steps of: (a) providing an electrostimulation device, the device adapted to deliver to a user a transcutaneous or percutaneous nerve electrostimulation signal; (b) in a first round of calibration, delivering an electrostimulation signal to the user through the electrostimulation device; (c) obtaining feedback from the user to determine whether the user senses a stimulus from the electrostimulation signal; (d) if the user does not sense the stimulus from the electrostimulation signal, increasing the intensity of the electrostimulation signal by a level equal to a first signal variation; (e) repeating steps (c) and (d) until the user senses the stimulus from the electrostimulation signal; (f) once the user senses a stimulus from the electrostimulation signal, concluding the first round of calibration; (g) in a second round of calibration, reducing the intensity of the electrostimulation signal sensed by the user at the conclusion of the first round of calibration, the level of reduction being equal to the first signal variation, and delivering the reduced electrostimulation signal to the user through the electrostimulation device; (h) obtaining feedback from the user to determine whether the user senses a stimulus from the electrostimulation signal; (i) if the user does not sense the stimulus from the electrostimulation signal, increasing the intensity of the electrostimulation signal by a level equal to a second signal variation, the second signal variation level being smaller than the first signal variation level; (j) repeating steps (h) and (i) until the user senses the stimulus from the electrostimulation signal; (k) once the user senses a stimulus from the electrostimulation signal, concluding the second round of calibration; and (l) reducing the intensity of the electrostimulation signal sensed by the user at the conclusion of the second round of calibration, the level of reduction being equal to the second signal variation, and delivering the reduced electrostimulation signal to the user through the electrostimulation device.

In an additional embodiment of the present invention, also disclosed are the following additional steps: conducting subsequent rounds of calibration in substantially the same manner as the first and second rounds of calibration, each successive round of calibration having a signal variation level that is smaller than the immediately preceding round of calibration; once the user senses a stimulus from the electrostimulation signal in a final round of calibration, concluding the final round of calibration: reducing the intensity of the electrostimulation signal sensed by the user at the conclusion of the final round of calibration, the level of reduction being equal to the signal variation used during the final round of calibration, and delivering the reduced electrostimulation signal to the user through the electrostimulation device; wherein the total number of rounds of calibration is an integer greater than 2.

DETAILED DESCRIPTION OF THE INVENTION

Figure 1:
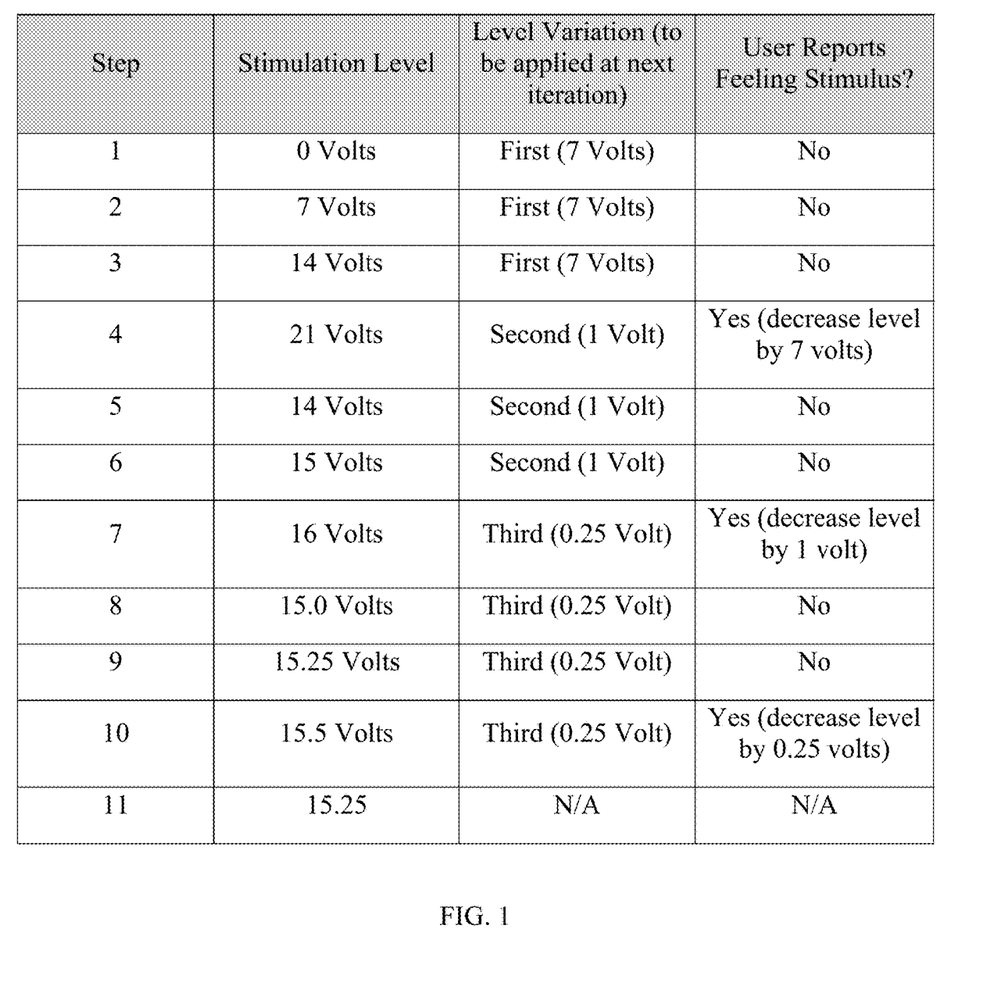
FIG. 1 is a table providing an example of the stimulation levels and user responses during an exemplary calibration session conducted in accordance with an embodiment of the present invention.

Referring to FIG. 1, illustrated is a table providing the exemplary application of various stimulation levels, and resulting user responses, during a calibration session for a VNS device conducted in accordance with an embodiment of the present invention. In the illustrated example there are three level variations in use: 7 volts, 1 volt, and 0.25 volts. At each step during the calibration process the VNS device delivers a stimulation signal to the user and the user is asked to report whether the stimulus is felt. Depending on the response of the user, the stimulation level is increased or decreased, and the process is repeated. After several iterative steps, a Sensory Threshold is determined.

In the example illustrated in FIG. 1, at Step 1 the user initially receives no stimulation (0 volts) and is asked to report whether any stimulus is felt. The user reports no feeling and therefore, at Step 2, the stimulation level is increased by the first variation level (7 volts) to a stimulation of 7 volts. The user is again asked to report any sensation. The user again reports no feeling and therefore, at Step 3, the stimulation level is increased by the first variation level (7 volts) to a stimulation of 14 volts. The user again reports no feeling and therefore, at Step 4, the stimulation level is increased by the first variation level (7 volts) to a stimulation of 21 volts.

Upon application of the 21-volt stimulus in Step 4, the user finally reports sensation. Accordingly, at Step 5, the stimulation level is decreased by the first variation level (7 volts) to a stimulation of 14 volts and the user is asked to confirm there is no sensation. Upon such confirmation, at Step 6, the stimulation level is increased by the second variation level (1 volt) to a stimulation of 15 volts. The user is asked to report any sensation. The user reports no sensation and, therefore, at Step 7, the stimulation level is increased by the second variation level (1 volt) to a stimulation of 16 volts. The user is asked to report any sensation.

Upon application of the 16-volt stimulus in Step 7, the user again reports feeling the stimulus. Accordingly, at Step 8, the stimulation level is decreased by the second variation level (1 volt) to a stimulation of 15 volts and the user is asked to confirm there is no sensation. Upon such confirmation, at Step 9, the stimulation level is increased by the third variation level (0.25 volts) to a stimulation of 15.25 volts. The user is again asked to report any sensation. The user reports no sensation and, therefore, at Step 10, the stimulation level is increased by the third variation level (0.25 volts) to a stimulation of 15.5 volts. The user is asked to report any sensation.

Upon application of the 15.5-volt stimulus in Step 10 the user again reports feeling the stimulus. Accordingly, at Step 11, the final step in this example, the stimulation level is decreased by the third variation level (0.25 volt) to a stimulation of 15.25 which is determined to be the Sensory Threshold in this example.

It can be easily appreciated that for this particular user the precise Sensory Threshold is a value between 15.25 and 15.5 volts. Greater precision in the calculation of the Sensory Threshold value could be achieved by additional rounds of calibration with decreasing variation levels below 0.25 volts (e.g., a round with variations of 0.1 volts, followed by a round with variations of 0.05 volts).

It should also be appreciated that the user need not be shown or told the actual level of the stimulation being provided at each step. The user need only be told that a stimulus is being provided and then asked to report whether he/she feels the stimulus. Similarly, once the Sensory Threshold is calculated, it is not necessary for the user to know the actual stimulus level (i.e., the voltage) corresponding to the Sensory Threshold.

It is, of course, useful to associate that final Sensory Threshold with the particular user so that the next time the user utilizes the VNS device the user can begin a treatment session without having to calculate the Sensory Threshold. For this purpose, it is envisioned that the VNS device will incorporate, or have access to, a mechanism for the user to uniquely identify itself (such as a username and password, or a biometric authentication) and a database that provides a corresponding value for the Sensory Threshold for the identified user.

In some embodiments of the present invention, it may be desirable to provide the user with some indication of the actual level of stimulation, including ultimately the value of the Sensory Threshold, without actually providing a voltage level. In such embodiments, the user may, for example, be provided a value for the stimulation being applied in terms relative to the maximum and minimum levels of stimulation that can be delivered by the VNS device.

One such embodiment is illustrated in FIG. 2 and FIGS. 3A-3F in which are shown (i) a table providing the second exemplary application of various stimulation levels, and resulting user responses, during a calibration session for a VNS device conducted in accordance with an embodiment of the present invention, and (ii) a sequence of screenshots of the electronic display of the VNS during the session.

In the example illustrated by FIGS. 2, and 3A-3F, there are four level variations in use, all expressed as a percentage of the maximum stimulation: 5%, 2%, 1% and 0.5%. As in the previous example, at each step during the calibration process the VNS device delivers a stimulation signal to the user and the user is asked to depress a button (physical or touchscreen) on the VNS device, or through an interface in communication with the VNS device, indicating whether the stimulus is felt. Depending on the response of the user, the stimulation level is increased or decreased, and the process is repeated. After several iterative steps, a Sensory Threshold is determined.

In the example illustrated in FIGS. 2, and 3A-3F, at Step 1 the user initially receives no stimulation (0%) (See FIG. 3A) and is asked to depress the (±) button until a sensation is felt. It is shown in Steps 2-12 that the user depressed the (+) button repeatedly, each press increasing the stimulation by 5% until it reached 60% when the sensation is felt (See FIG. 3B).

At this point, in Step 13, the user depressed the "Participant Feels Sensation" button, which reduces the stimulus by the first variation level (5%) to 55% and the user is asked to confirm the inability to feel a sensation by depressing the "Participant No Longer Feels Sensation" button. (See FIG. 3C). It should be noted that if the user does feel a sensation, he can press the (−) button which will decrease the stimulation by the first variation (5%) again and repeat the process.

Figure 2:
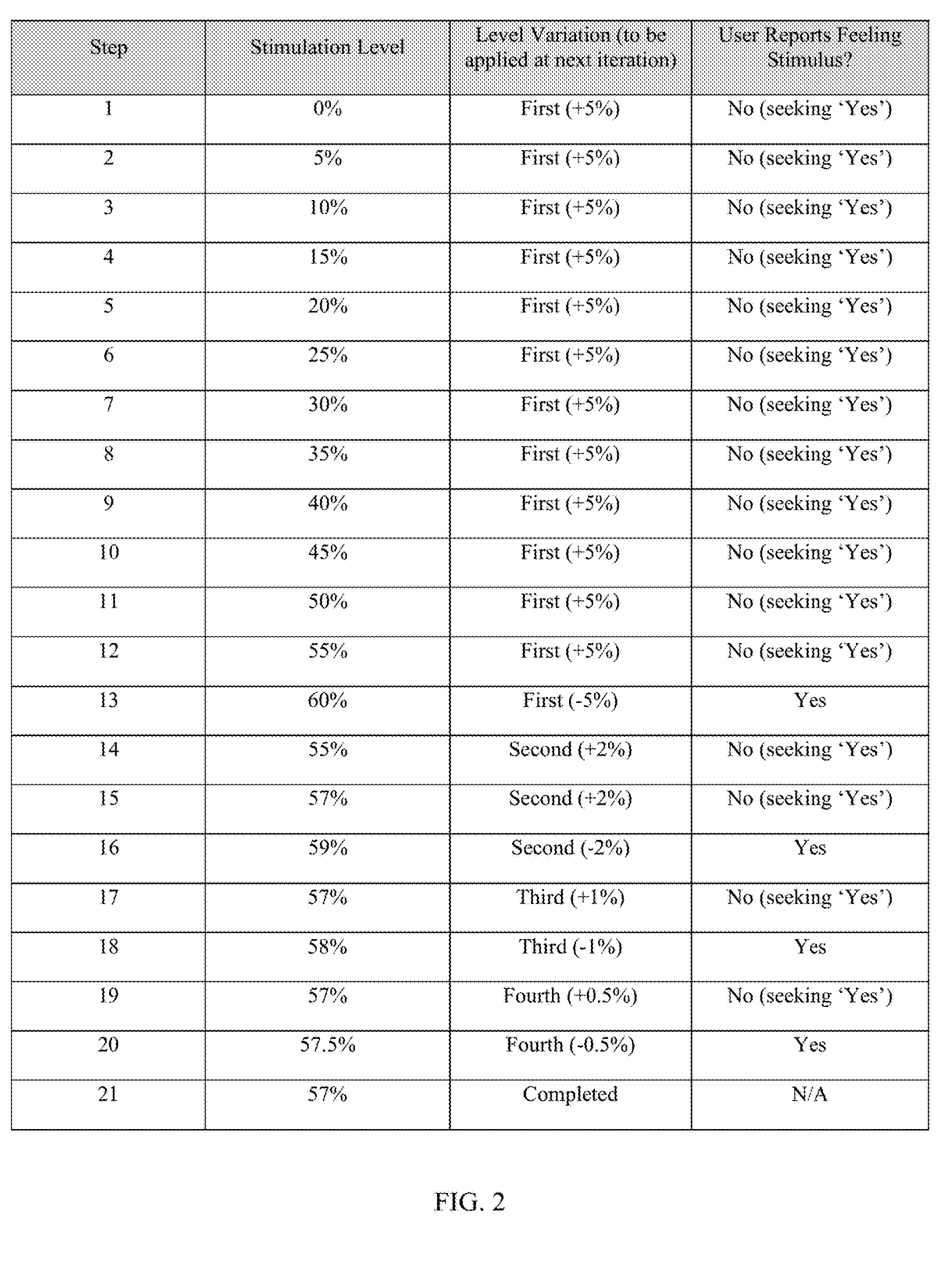
FIG. 2 is a table providing an example of the stimulation levels and user responses during a second exemplary calibration session conducted in accordance with an embodiment of the present invention.
Figure 3A:
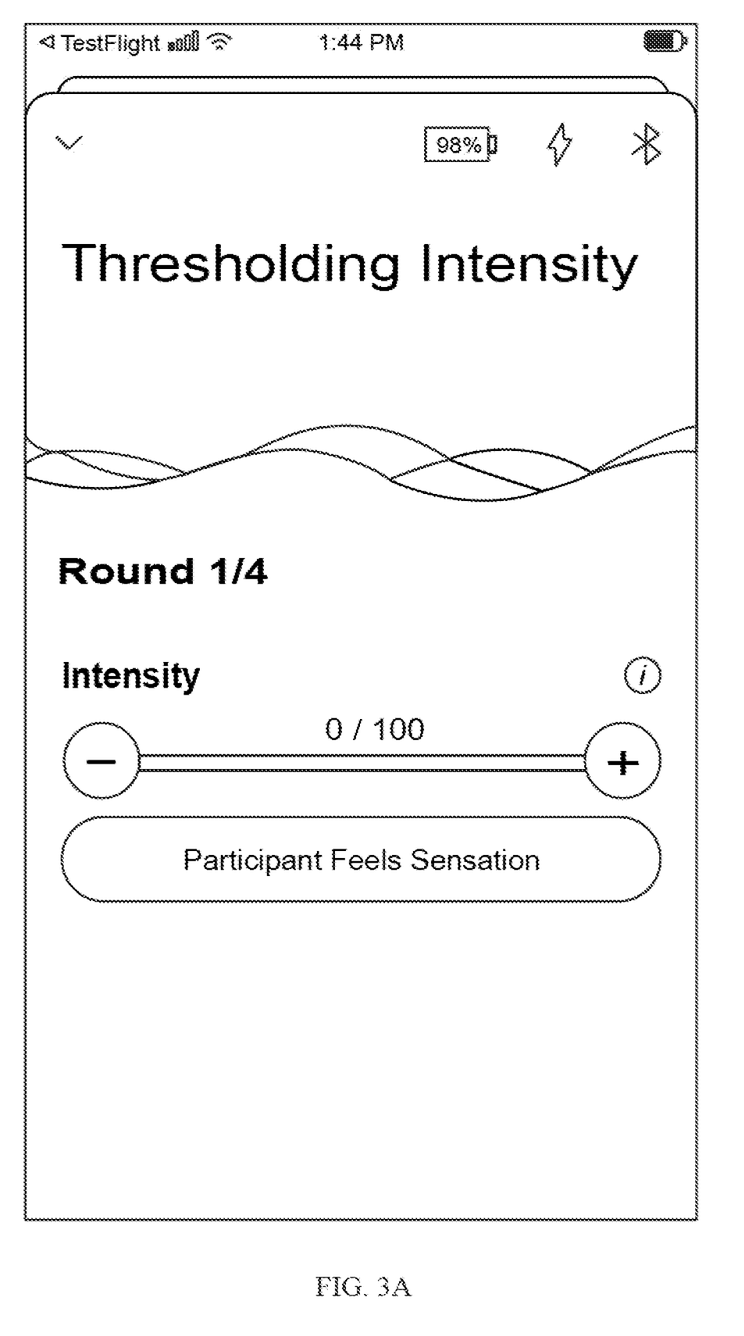
FIGS. 3A-3F illustrate a sequence of screenshots of a digital display in a VNS device during the second exemplary calibration represented in FIG. 2.
Figure 3B:
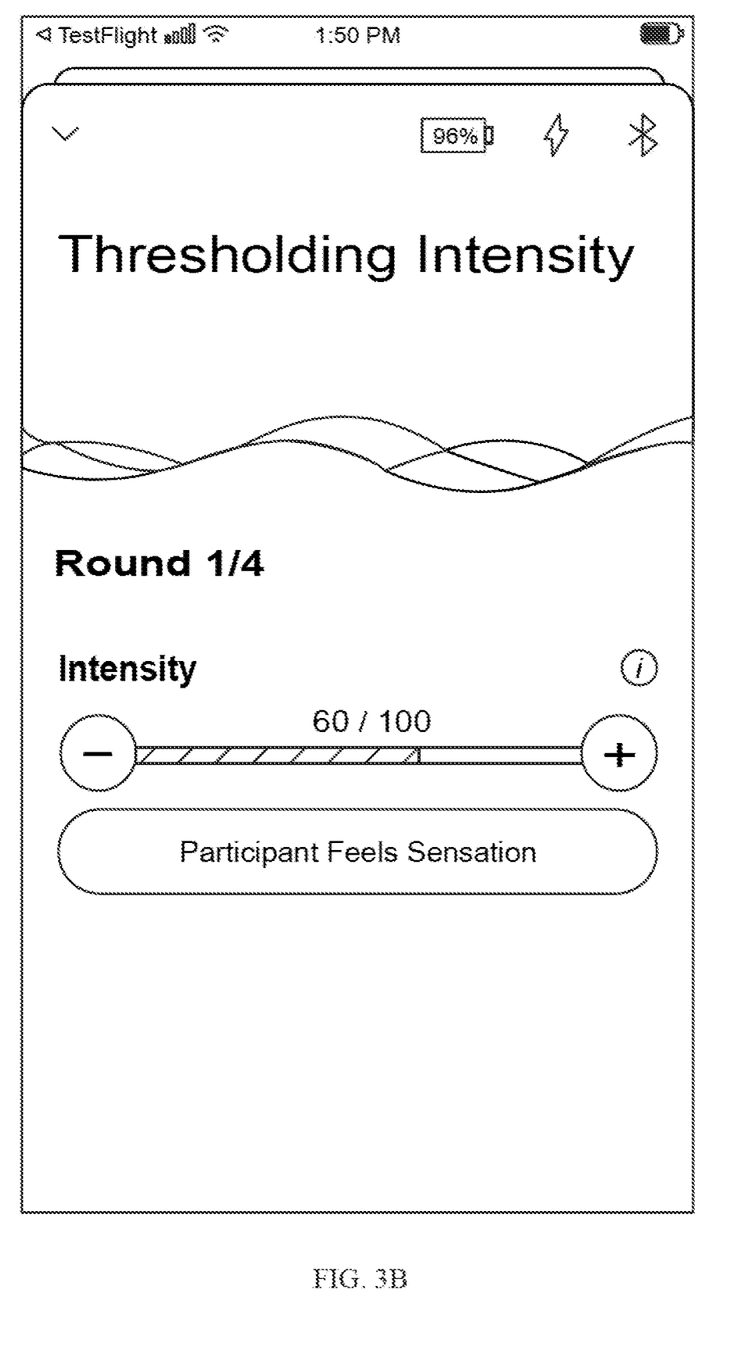
Figure 3C:
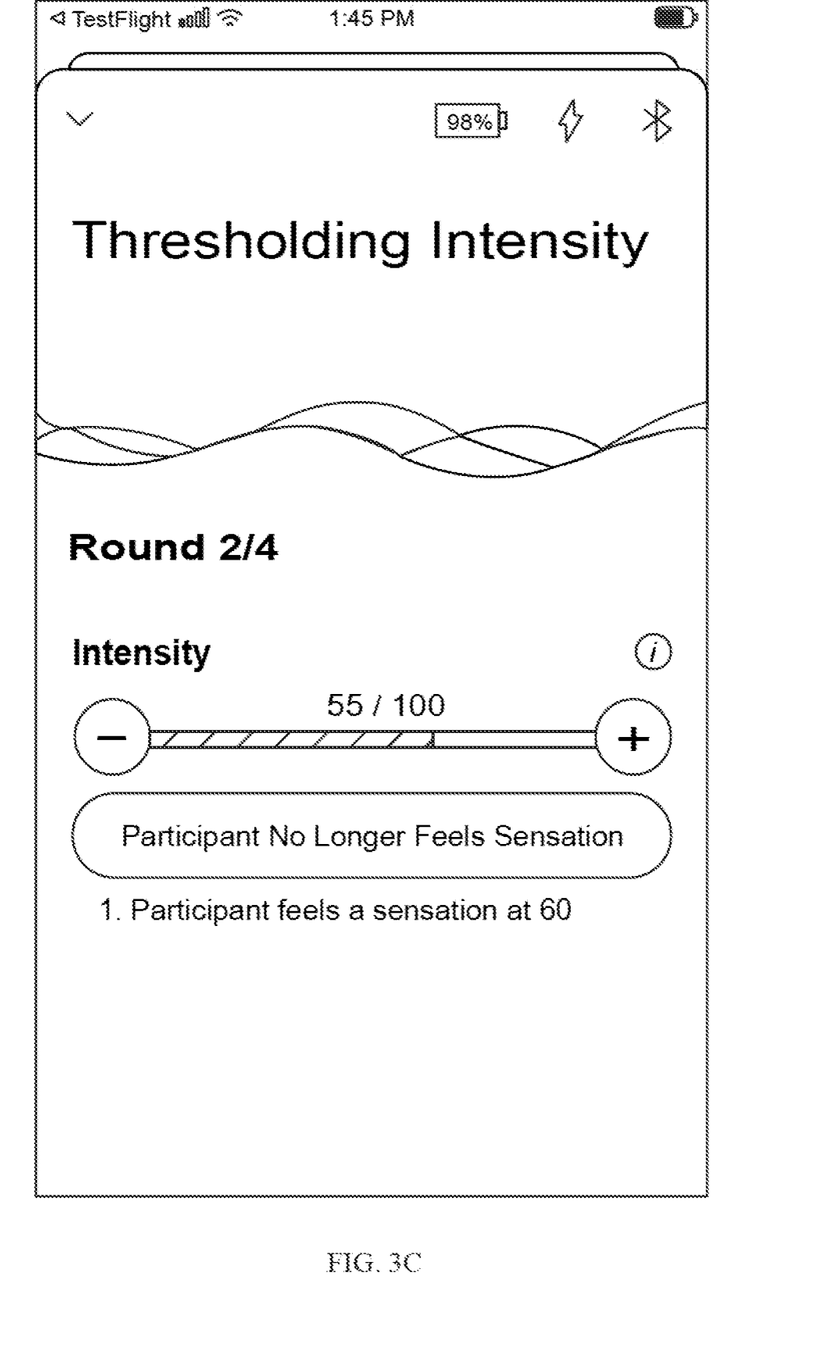
Figure 3D:
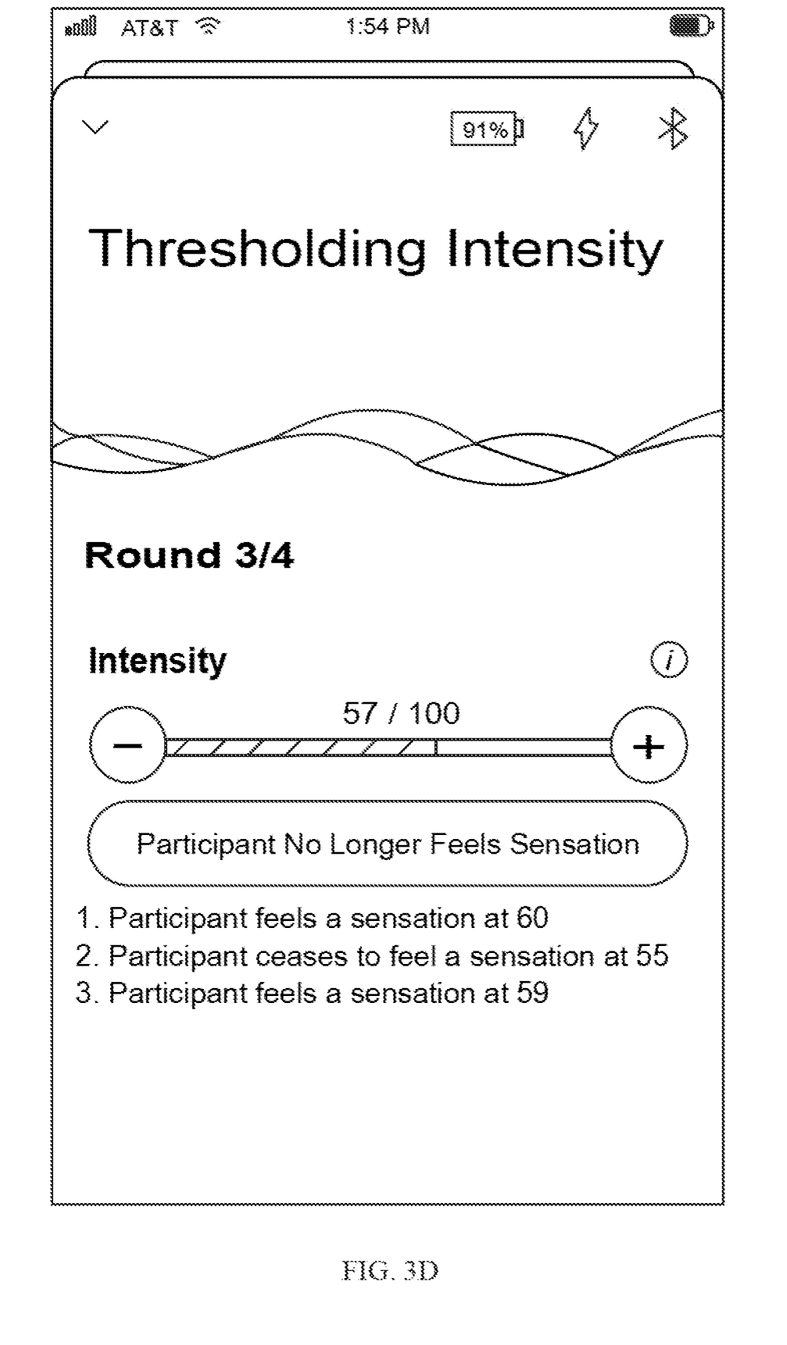
Figure 3E:
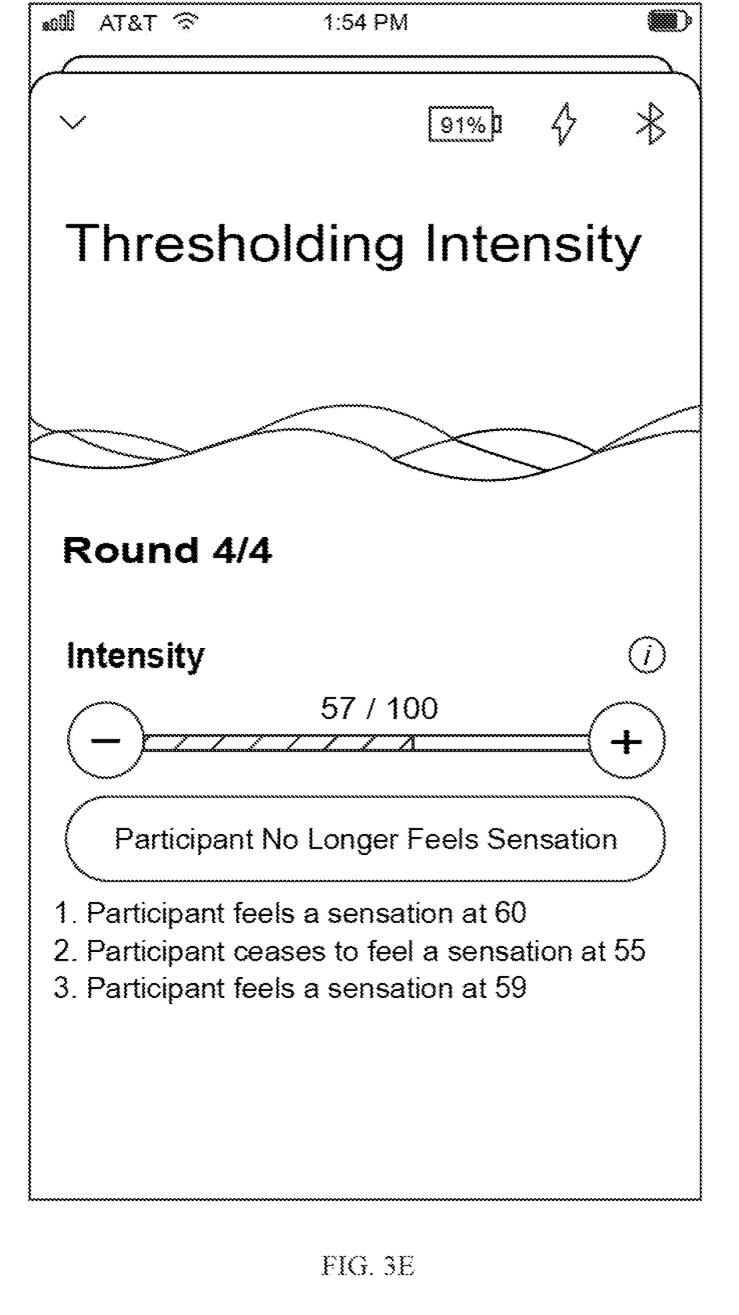
Figure 3F:
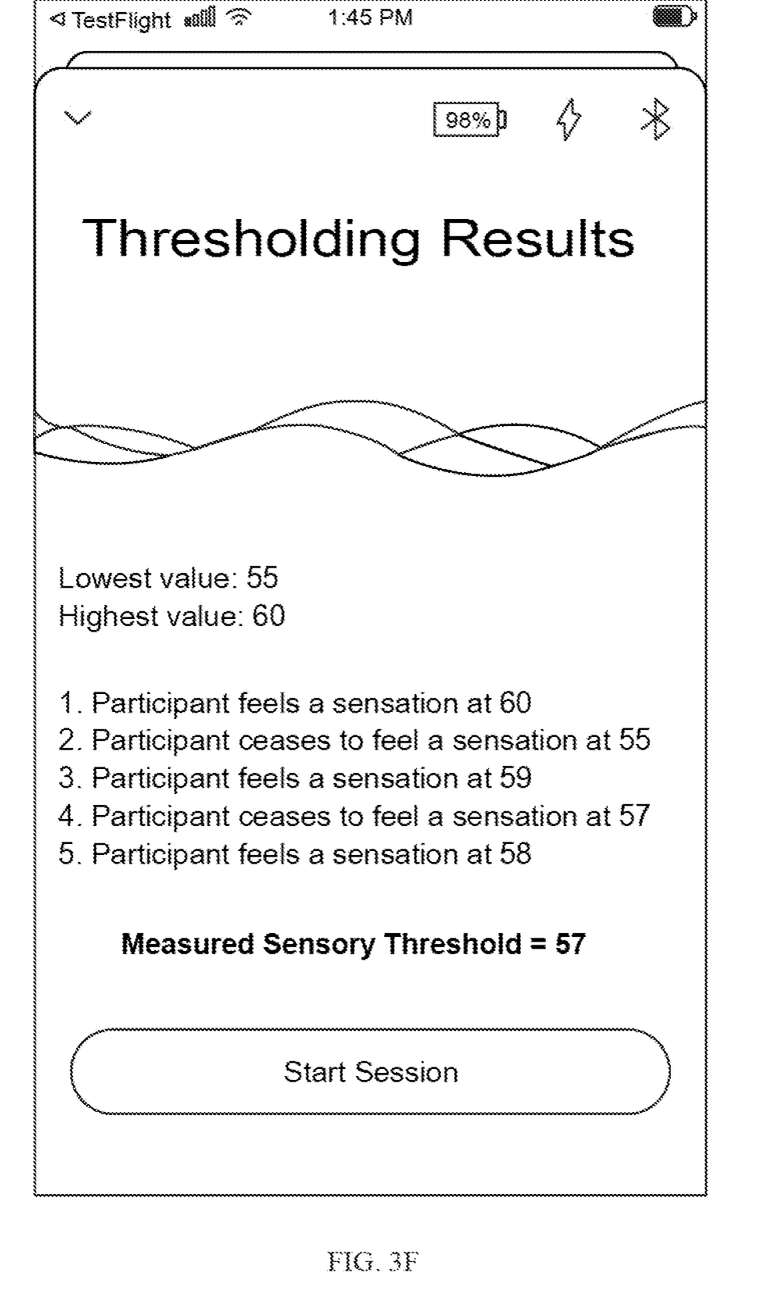

As shown in FIG. 2 at Steps 14-15, the user did not feel the stimulus and so it depressed the (+) twice, until the stimulus was felt. Each press of the button increased the stimulus by the second variation (2%) to reach a stimulation level of 59%. At Step 16 the user again feels the stimulus and accordingly presses the "Participant Feels Sensation" button which reduces the stimulus by the second variation level (2%) to 57% and the user is asked to confirm the inability to feel a sensation by depressing the "Participant No Longer Feels Sensation" button. (See FIG. 3D).

Next, at Step 17, the user does not feel the stimulus at 57% and depresses the (+) button which increases the stimulus by the third variation level (1%) to 58%. At Step 18 the user again feels the stimulus and accordingly presses the "Participant Feels Sensation" button which reduces the stimulus by the third variation level (1%) to 57%. At Step 19, the user is asked to confirm the inability to feel a sensation by depressing the "Participant No Longer Feels Sensation" button. (See FIG. 3E). When the user does not feel the stimulus, he depresses the (+) button and the stimulation is increased by the fourth variation level (0.5%) to 57%. Finally, at Step 20, the user reports feeling the stimulus at 57.5% by pressing the "Participant Feels Sensation" button, which reduces the stimulus by the fourth variation level (0.5%) to 57%. At Step 21, the Sensory Threshold is determined to be 57% and the user is given the option to start a session using that value (See FIG. 3F).

Optionally, a safety margin can be assigned to the user Which reduces the stimulus level to a certain percentage, or voltage, below the measured Sensory Threshold. Also optionally, lower and upper Sensory Thresholds can be established for the user by reducing and increasing the measured Sensory Threshold by set voltage intensity levels.

It can be easily observed that if additional rounds were conducted using smaller level variations for each subsequent round, the ST could be determined with greater precision than 0.5%. Any inconsistency in responses from the user would require a recheck by another crossing until resolved with two or more consistent consecutive crossings. The threshold would then be stored for future use or recall in connection with the user. The VNS device can then be set to provide stimulation at the ST, above the ST, or below the ST, depending on the type of therapy or testing being administered. If the user was part of a control group, the user's ST would be normally calibrated, but once calibration is done would only receive the control stimulus, or no stimulus, as appropriate.

Although the above examples illustrate embodiments that request explicit feedback from the user to report when the stimulus is sensed, the process can be fully automated by measuring one or more biofeedback parameters from the user through built in, or external sensors. Exemplary biofeedback parameters that could be used to detect when the sensory level has been reached by the user include:

Heart rate
Feeling perception
Heart rate variability
Blood pressure
$VO_2$ max
Stress level.
Sleep quality
Cardiac efficiency
Focus or concentration
Neuroplasticity
Hydration level
Hypertension indicator
Cardiovascular trends
LF/HF Ratio
Respiration Rate
$SpO_2$
Pulmonary Function Tests Facial Expression
Pupillometry
Galvanic Skin Response
EMG
EEG Moreover, although the interface input control described in the examples for the user to provide feedback is one or more labeled buttons (either physical or virtual, such as in a touchscreen) additional interface input control types, such as voice and sound sensors, movement sensors, and similar interface input control types be used.

In addition, although the above-described examples utilize voltage intensity as the stimulus that is the variable, or user-variable, output, a variety of other output parameters can be varied to provide stimulation. These include:

Pulse width
Peak voltage
Average voltage
Pulse latency or spacing
Frequency
Peak current
Average current
Offset current (a non-zero DC offset voltage)
Carrier wave characteristics
Audio volume
Polarity of stimulation While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the described embodiments, features, benefits, methods, and examples, but by all embodiments and methods within the scope and spirit of the invention as described and claimed.

For example, the above methods could be used to calibrate a VNS device for a different type of threshold. One example is a "pain" threshold at which a user would feel pain from the stimulus. In such calibration the user would be asked if he/she feels pain, rather than if they feel any stimulus. Once the pain threshold is calculated the VNS device can be programmed to not stimulate at or above such level in order to avoid discomfort or injury to the user.

We claim:

1. A method for calibrating a nerve electrostimulation device, the method comprising the steps of:
   a. providing an electrostimulation device, the device adapted to deliver to a user a transcutaneous or percutaneous nerve electrostimulation signal;
   b. in a first round of calibration, delivering an electrostimulation signal to the user through the electrostimulation device;
   c. obtaining feedback from the user to determine whether the user senses a stimulus from the electrostimulation signal;
   d. if the user does not sense the stimulus from the electrostimulation signal, increasing the intensity of the electrostimulation signal by a level equal to a first signal variation;
   e. repeating steps (c) and (d) until the user senses the stimulus from the electrostimulation signal;
   f. once the user senses a stimulus from the electrostimulation signal, concluding the first round of calibration;
   g. in a second round of calibration, reducing the intensity of the electrostimulation signal sensed by the user at the conclusion of the first round of calibration, the level of reduction being equal to the first signal variation, and delivering the reduced electrostimulation signal to the user through the electrostimulation device;
   h. obtaining feedback from the user to determine whether the user senses a stimulus from the electrostimulation signal;
   i. if the user does not sense the stimulus from the electrostimulation signal, increasing the intensity of the electrostimulation signal by a level equal to a second signal variation, the second signal variation level being smaller than the first signal variation level;
   j. repeating steps (h) and (i) until the user senses the stimulus from the electrostimulation signal;
   k. once the user senses a stimulus from the electrostimulation signal, concluding the second round of calibration;
   l. reducing the intensity of the electrostimulation signal sensed by the user at the conclusion of the second round of calibration, the level of reduction being equal to the second signal variation, and delivering the reduced electrostimulation signal to the user through the electrostimulation device.

2. The method for calibrating a nerve electrostimulation device of claim 1, the method comprising the further steps of:
   conducting subsequent rounds of calibration in substantially the same manner as the first and second rounds of calibration, each successive round of calibration having a signal variation level that is smaller than the immediately preceding round of calibration;
   once the user senses a stimulus from the electrostimulation signal in a final round of calibration, concluding the final round of calibration;
   reducing the intensity of the electrostimulation signal sensed by the user at the conclusion of the final round of calibration, the level of reduction being equal to the signal variation used during the final round of calibration, and delivering the reduced electrostimulation signal to the user through the electrostimulation device;
   wherein the total number of rounds of calibration is an integer greater than 2.

3. The method for calibrating, a nerve electrostimulation device of claim 1 wherein the nerve electrostimulation device is adapted to stimulate one or more of the following nerves: vagus, trigeminal, facial, vestibulocochlear, and glossopharyngeal.

4. The method for calibrating a nerve electrostimulation device of claim 1 wherein the step of obtaining feedback from the user comprises the user to interacting with an input interface control.

5. The method for calibrating a nerve electrostimulation device of claim 1 wherein the step of obtaining feedback from the user comprises measuring one or more biofeedback parameters from the user.

* * * * *